United States Patent [19]

Feyen et al.

[11] Patent Number: 4,607,108
[45] Date of Patent: Aug. 19, 1986

[54] PROCESS FOR THE PREPARATION OF 3-ISOMERS OF 1-CYCLOHEXYL-2-(1,2,4-TRIAZOL-1-YL)-1-PENTEN-3-ONE DERIVATIVES

[75] Inventors: Peter Feyen, Mettmann, Fed. Rep. of Germany; Gebhard Rauleder, Belford Roxo, Brazil; Wolf Reiser, Wuppertal, Fed. Rep. of Germany

[73] Assignee: Bayer Aktiengesellschaft, Leverkusen, Fed. Rep. of Germany

[21] Appl. No.: 623,800

[22] Filed: Jun. 22, 1984

[30] Foreign Application Priority Data

Jun. 24, 1983 [DE] Fed. Rep. of Germany ....... 3322818

[51] Int. Cl.$^4$ ........................................... C07D 249/08
[52] U.S. Cl. ..................................................... 548/262
[58] Field of Search ........................................ 548/262

[56] References Cited

U.S. PATENT DOCUMENTS 4,486,218  12/1984  Reiser et al. .................... 548/262
4,501,897   2/1985  Reiser et al. .................... 548/262

Primary Examiner—Alton D. Rollins
Attorney, Agent, or Firm—Sprung Horn Kramer & Woods

[57] ABSTRACT

The known E-isomers of compounds of the formula

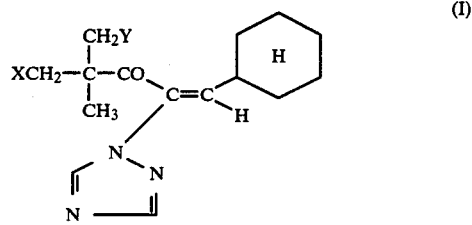

in which
X and Y independently of each other represent hydrogen or halogen, are obtained according to a new process, in which triazolylketones of the formula

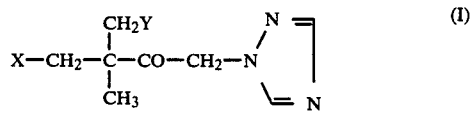

in which
X and Y have the above mentioned meaning, are reacted with an excess of cyclohexanecarbaldehyde in the presence of a non-polar organic diluent and in the presence of a catalyst mixture of organic acids and secondary amines in a molar ratio of 1:0.5 to 1:1 at temperatures between 40° and 100° C. by continuously removing the water formed and subsequently working up in the manner that is described in the specification.

4 Claims, No Drawings

PROCESS FOR THE PREPARATION OF 3-ISOMERS OF 1-CYCLOHEXYL-2-(1,2,4-TRIAZOL-1-YL)-1-PENTEN-3-ONE DERIVATIVES

The present invention relates to a new process for preparing known plant-growth-regulating and fungicidally active E-isomers *) of 1-cyclohexyl-2-(1,2,4-triazol-1-yl)-1-penten-3-one derivatives.

*) "E-isomers" are to be understood as meaning in the present case those 1-cyclohexyl-2-(1,2,4-triazol-1-yl)-1-penten-3-one derivatives in which the cyclohexyl radical and the 1,2,4-triazolyl radical are on 'entgegengesetzten' ("opposite") sides of the double bond.

It has already been disclosed that 1-cyclohexyl-2-(1,2,4-triazol-1-yl)-penten-3-one derivatives are obtained when cyclohexanecarbaldehyde is reacted with appropriate triazolyl-ketones in the presence of a basic catalyst, such as, for example, piperidine acetate and in the presence of an inert organic solvent, in particular in the presence of an (aromatic) hydrocarbon, at the boiling point of the particular solvent.

The end products, in this case in particular the various isomers, are preferably isolated by way of their acid addition salts (compare European Preliminary Published Application No. 15,387).

This process has the disadvantage that the preparation of pure isomers, such as in particular of the E-isomers, proceeds in an economically unfavourable manner. Thus, liberation of the particular pure isomer from the corresponding acid addition salt by means of a base, such as, for example, sodium carbonate, requires a change of solvent, and yields of the isomeric product desired are generally unsatisfactory.

It has now been found that the known E-isomers of 1-cyclohexyl-2-(1,2,4-triazol-1-yl)-1-penten-3-one derivatives of the formula

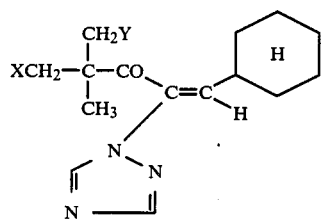

(I)

in which
X and Y independently of each other represent hydrogen or halogen,
are obtained when triazolyl-ketones of the formula

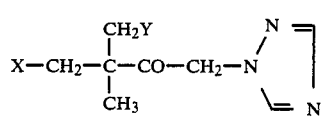

(II)

in which
X and Y have the above mentioned meaning, are reacted with an excess of cyclohexanecarbaldehyde of the formula

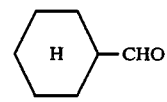

(III)

in the presence of a non-polar organic diluent and in the presence of a catalyst mixture of organic acids and secondary amines in a molar ratio of 1:0.5 to 1:1 at temperatures between 40° and 100° C. by continuously removing the water formed and then either (a) an aqueous base is added to the reaction mixture, which, if appropriate after the aqueous phase has been separated off, is stirred at temperatures between −20° C. and +30° C., and the product precipitating in the form of crystals is separated off, or (b) the reaction mixture is treated in any order first of all with an aqueous mineral acid and an aqueous base and then washed with water, the organic phase is then concentrated by distilling out excess cyclohexanecarbaldehyde and solvent, the remaining residue, if appropriate after prior distillation, is reacted at temperatures between −20° C. and +30° C. with secondary amines, if appropriate in the presence of water and/or in the presence of a water-non-miscible solvent, and the product precipitating in the form of crystals in the course of the reaction is separated off.

It has to be called extremely surprising that the E-isomers of 1-cyclohexyl-2-(1,2,4-triazol-1-yl)-1-penten-3-one derivatives of the formula (I) can be prepared in signficantly higher yields by the process according to the invention than by the previous process known for synthesising these substances.

The process according to the invention has a number of advantages over the prior-known method of preparing the E-isomers of compounds of the formula (I). Thus, the process according to the invention requires only relatively short reaction times and relatively small amounts of solvent. In addition, there is no need to change the solvent between the reaction itself and the working-up. The desired products are obtained in very high yields and in excellent purity virtually free of interfering by-products. Isolating the substances prepared according to the invention presents no problem, since they can be separated from the reaction mixture by simply filtering with or without suction. A further significant advantage of the process according to the invention finally is that unreacted cyclohexanecarbaldehyde and the mixture of organic acid and secondary amine, which serves as the catalyst, can be recovered.

The E-isomers of 1-cyclohexyl-2-(1,2,4-triazol-1-yl)-1-penten-3-one derivatives which can be obtained by the process according to the invention are defined by the formula (I). In this formula, X and Y independently of each other preferably represent hydrogen, fluorine, chlorine or bromine.

In particularly preferred compounds of the formula (I), X represents hydrogen and Y represents hydrogen, fluorine or chlorine.

The compounds which can be prepared according to the invention, their plant-growth-regulating or fungicidal properties, and the use of these substances as intermediate products for preparing other plant growth regulators and fungicides are known (cf. European Preliminary Published Application No. 15,387).

If 3,3-dimethyl-1-(1,2,4-triazol-1-yl)-butan-2-one and cyclohexanecarbaldehyde are used as starting materials, a mixture of piperidine and benzoic acid is used as the catalyst, isododecane is used as the diluent and dimethylamine is used as the secondary amine in the crystallisation, then the course of the process according to the invention can be represented by the following reaction equation:

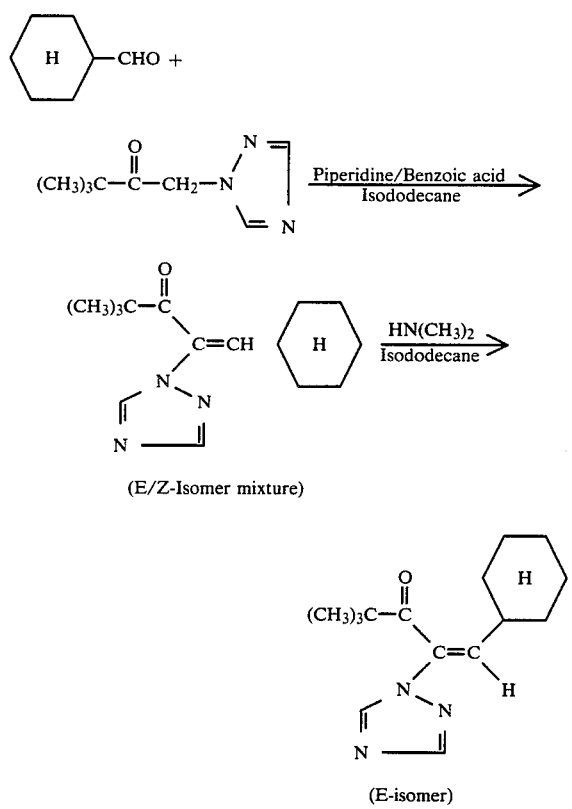

(E/Z-Isomer mixture)

(E-isomer)

The triazolyl-ketones required as starting materials for carrying out the process according to the invention are defined by the formula (II). In this formula, X and Y preferably represent those radicals which have already been mentioned as preferable for these substituents in connection with the description of the substances of the formula (I), which can be prepared according to the invention.

The triazolyl ketones of the formula (II) are known (cf. European Preliminary Published Application No. 15,387).

The cyclohexanecarbaldehyde of the formula (III) required as a reaction component for carrying out the process according to the invention is likewise known.

The diluent used in carrying out the process according to the invention can be any non-polar organic solvent. It is preferably isobutanol, xylene, toluene, cyclohexane, ligroin, isooctane, dodecane or isododecane.

In the process according to the invention, a mixture of an organic acid and a secondary amine serves as the catalyst. The organic acids used in the mixture are preferably acetic acid, propionic acid, pivalic acid, 2-ethylhexanoic acid, cyclohexane carboxylic acid and benzoic acid. The secondary amine is preferably dimethylamine, diethylamine, diisopropylamine, diisobutylamine, pyrrolidine, morpholine, hexahydro-1-H-azepine, piperidine, 2-methylpiperidine or 2,6-dimethylpiperidine.

In the catalyst mixture, the ratio of organic acid to secondary amine can be varied within a specific range. In general, 0.4 to 1 mole, preferably 0.5 to 0.9 mole, of secondary amine is used per mole of organic acid.

The reaction temperatures for the reaction according to the invention can be varied within a specific range. In general, the reaction is carried out at temperatures between 40° C. and 100° C., preferably between 50° C. and 80° C.

In carrying out the process according to the invention, the reaction is performed either under atmospheric pressure or even under reduced pressure, for example under pressures between 5 and 100 mbar, preferably between 10 and 50 mbar. The latter is especially expedient if the reaction temperatures used are relatively low and if the solvents used have relatively high boiling points.

In the course of carrying out the reaction according to the invention, the water formed is continuously removed from the reaction mixture. In general this is done by means of a water separator. However, it is also possible to bind in the reaction mixture the water formed by adding suitable materials, such as, for example, molecular sieves.

The reaction times for the reaction according to the invention can be varied within a relatively wide range. The duration of the reaction is generally between 3 and 20 hours, preferably between 4 and 14 hours.

In carrying out the process according to the invention, the triazolyl-ketones of the formula (II) are reacted with an excess of cyclohexanecarbaldehyde of the formula (III). In general, 1.1 to 1.8 moles, preferably 1.15 to 1.6 moles of cyclohexanecarbaldehyde of the formula (III) are used per mole of triazolyl-ketone of the formula (II). The amount of catalyst mixture can likewise be varied within a specific range. In general, between 0.05 and 0.5 mole, preferably between 0.1 and 0.3 mole, of organic acid and between 0.05 and 0.3 mole, preferably between 0.05 and 0.2 mole, of secondary amine is used per mole of triazolyl-ketone of the formula (II). Even the amount of non-polar organic diluent can be varied within a specific range. The process can also be carried out in the absence of a solvent. In general, 0 to 1,200 g, preferably 50 to 500 g, of solvent are used per mole of triazolyl-ketone of the formula (II).

The reaction according to the invention is carried out in detail by putting together the starting materials, the catalyst components and the solvent in the specified amounts and ensuring, by stirring and/or boiling, if appropriate under reduced pressure, that the mixture is thoroughly mixed. It has been found to be advantageous to carry out this stage by putting the triazolyl-ketone of the formula (II), the catalyst acid and the non-polar solvent into the reaction vessel first and to add a mixture of cyclohexanecarbaldehyde of the formula (III) and catalyst base (secondary amine) within a period of 0.5 to 2 hours.

It can be technically advantageous first to distil some of the water out of the mixture of cyclohexanecarbaldehyde and catalyst base, and then to meter in the dehydrated mixture.

When the reaction has ended and the reaction mixture has cooled down to 20° to 40° C., there are two possible variants, (a) and (b), for the working-up.

In working in accordance with variant (a), the general procedure is that an aqueous base, preferably a dilute aqueous alkali metal base, such as, for example, sodium hydroxide solution or potassium hydroxide solution, is added to the reaction mixture, the two are thoroughly mixed, and, if appropriate after prior separating out of the aqueous phase, the resulting mixture is cooled with thorough stirring to temperatures between −20° C. and +30° C., preferably between −10° C. and +10° C. The desired products precipitate in the form of crystals and can be separated by filtering with or without suction and be isolated in the pure form by washing with a little cold organic solvent and subsequently drying. If desired, the products can be freed from any impurities still present by recrystallisation. Additional product can be obtained in the form of crystals from the filtrate remaining after the isolation of the crystalline product, by successively washing with aqueous mineral acid, such as, for example, sulphuric acid, dilute aqueous base, such as, for example, sodium hydroxide solution or potassium hydroxide solution and water as well as after further concentrating of the organic phase, if appropriate after addition of a secondary amine, such as, for example, dimethylamine or piperidine, and by stirring at low temperatures.

In working in accordance with variant (b), the general procedure is that first of all the reaction mixture is extracted with aqueous mineral acid, such as, for example, sulphuric acid, and with dilute aqueous base, preferably an alkali metal base, such as, for example, sodium hydroxide solution or potassium hydroxide solution, this process is repeated if necessary, and the organic phase is then washed with water. Afterwards the organic phase is concentrated by distilling off excess cyclohexanecarbaldehyde and solvent, and the residue remaining behind, if appropriate after prior distillation, has added to it, at temperatures between −20° C. and +30° C., preferably between −10° C. and +10° C., a secondary amine, such as, for example, dimethylamine, diethylamine, pyrrolidine or piperidine, if appropriate in the presence of water and/or in the presence of a water-non-miscible solvent, such as, for example, xylene, toluene, cyclohexane, ligroin, isooctane, dodecane or isododecane, and the mixture is thoroughly stirred. In the course of the stirring, the desired products precipitate in the form of crystals, and can be separated off by filtering with or without suction and can be isolated in the pure form by washing with a little cold organic solvent and subsequently drying. If the crystallisation is carried out in water, it is often advantageous to add an emulsifier. Any impurities still present can be removed by recrystallisation. Additional product can be obtained in the form of crystals in the above mentioned manner from the mother liquor remaining after the isolation of the crystalline product by further concentrating and making a further addition of secondary amine.

Solvent and cyclohexanecarbaldehyde distilled out in the course of the process according to the invention can be used again for reaction. The catalyst components can likewise by isolated in a simple way and re-used. This is generally done by first of all bringing the combined aqueous phases to pH 12 by adding aqueous alkali metal hydroxide, for example sodium hydroxide solution or potassium hydroxide solution, and distilling off secondary amine in the form of a mixture with water. In addition to separating the amine out by distillation, the amine can also be removed by extraction, for which the extractant used is advantageously a mixture of cyclohexanecarbaldehyde and the solvent used for the reaction. After replenishment of lost amine, the extracts can be directly used for renewed reaction. The bottoms remaining behind in the distillation are then brought to pH 1–4 by adding aqueous mineral acid, for example sulphuric acid, so that the catalyst acid is liberated and can be isolated either by distillation or extraction or—if it is a solid substance—by filtering with suction.

The process according to the invention can be carried out either discontinuously or continuously.

The process according to the invention is illustrated by the following examples.

COMPARATIVE EXAMPLE

Preparation of the E-isomer of 1-cyclohexyl-4,4-dimethyl-2-(1,2,4-triazol-1-yl)-1-penten-3-one of the formula

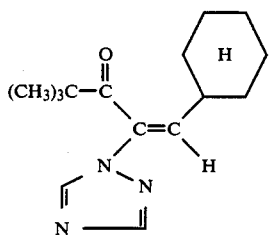

using the process described in European Preliminary Published Application No. 15,387.

A mixture of 83.5 g (0.5 mole) of 3,3-dimethyl-1-(1,2,4-triazol-1-yl)-butan-2-one, 60 g (0.54 mole) of cyclohexanecarbaldehyde, 4.2 g (0.05 mole) of piperidine and 6 g (0.1 mole) of glacial acetic acid in 300 ml of toluene are refluxed under a water separator until water is no longer separated off. When the reaction mixture had cooled down to room temperature it was washed with saturated aqueous sodium chloride solution. The organic phase was dried over sodium sulphate, filtered, and concentrated by drawing off the solvent under reduced pressure. The residue remaining behind was taken up in 500 ml of acetone, and a filtered solution of 90 g (0.25 mole) of naphthalene-1,5-disulphonic acid in 500 ml of acetone was added with stirring.

The initial precipitate was filtered off with suction, the filtrate was concentrated further, and the colourless crystalline residue obtained was taken up in 500 ml of ethylene chloride. Semi-concentrated aqueous sodium carbonate solution was then added until the reaction was alkaline. The organic phase was separated off, dried and filtered, and the filtrate was concentrated. The oily residue was taken up in petroleum ether and left to crystallise. This gave 64 g (49% by theory) of the E-isomer of 1-cyclohexyl-4,4-dimethyl-2-(1,2,4-triazol-1-yl)-1-penten-3-one in the form of a solid substance having a melting point of 98° C.

PREPARATION EXAMPLES ACCORDING TO THE INVENTION

EXAMPLE 1

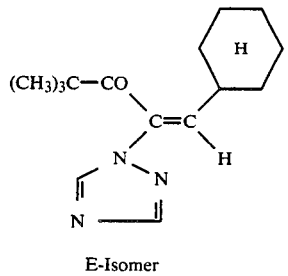

E-Isomer

A mixture of 10.8 moles of cyclohexanecarbaldehyde and 2.13 moles of piperidine was added dropwise at 65° C. under a pressure of 10 to 20 mbar in the course of 15 minutes to a mixture of 8 moles 3,3-dimethyl-1-(1,2,4-triazol-1-yl)-butan-3-one and 3.2 moles of cyclohexane carboxylic acid in 2.4 kg of isododecane. This mixture was likewise boiled under a pressure of 10 to 20 mbar and under a water separator for 12 hours, during which 185 g of water separated off. On cooling down to 40° C., the reaction mixture had added to it first of all 2 liters of water and then 90 ml of concentrated hydrochloric acid, so that the pH of the mixture was 5. The aqueous phase was separated off, and the organic phase was washed in succession with 1,408 g of 10% strength aqueous sodium hydroxide solution, with a mixture of 2 kg of water and 6 ml of concentrated hydrochloric acid, and with water. The organic phase thus obtained was concentrated by distilling off the cyclohexanecarbaldehyde still present and some solvent under reduced pressure. 40 g of dimethylamine were passed into the residue left behind at temperatures between −5° C. and 0° C. with thorough stirring in the course of 30 minutes. The resulting mass of crystals was kept stirrable by adding isododecane. After the mass of crystals had been stirred for 5 hours at temperatures between −5° C. and 0° C., the solid was filtered off with suction, and dimethylamine was again added to the mother liquor after the mother liquor had been concentrated to half its previous volume. The resulting crystalline product was likewise filtered off with suction and combined with the first crop of crystals obtained, and the combined crystals were washed with a little ice-cold isododecane. Drying at 50° C. in vacuo at this rate produced 1,876 g of a product which consisted to 98% of the E-isomer of 1-cyclohexyl-4,4-dimethyl-2-(1,2,4-triazol-1yl)-1-penten-3-one. The yield can accordingly be calculated as being 88% of theory.

Melting point: 99° C.

EXAMPLE 2

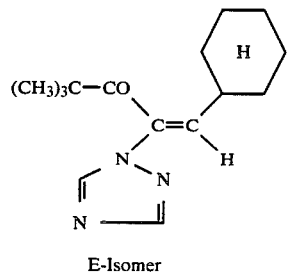

E-Isomer

A mixture of 1 mole of 3,3-dimethyl-1-(1,2,4-triazol-1-yl)-butan-3-one, 0.45 mole of benzoic acid, 1.3 moles of cyclohexanecarbaldehyde, 0.3 mole of piperidine and 300 g of isododecane was boiled at 70° C. under a pressure of about 20 mbar and under a water separator for 5 hours. When 22 ml of water had separated off, the mixture was worked up by adding water to the reaction mixture cooled down to 40° C. and then washing in succession with dilute aqueous hydrochloric acid, dilute sodium hydroxide solution and water. The organic phase thus obtained was concentrated by distilling off cyclohexanecarbaldehyde still present and some solvent. The remaining solution had added to it 26 g of a 10% strength solution of dimethylamine in isododecane and was stirred at temperatures between −10° C. and 0° C. for 12 hours. The solid product in the form of crystals was filtered off with suction, and dimethylamine in isododecane was again added to the mother liquor after the mother liquor had been concentrated to half its previous volume, and the solid precipitate was filtered off with suction. The combined crops of crystals were washed with a little isododecane and dried. This gave 231 g of a product which consisted to a 97% of the E-isomer of 1-cyclohexyl-4,4-dimethyl-2-(1,2,4,-triazol-1-yl)-1-penten-3-one. From this the yield can be calculated as being 85.8% of theory.

The combined aqueous phases were brought to pH 12 by adding aqueous sodium hydroxide solution and were subjected to a distillation. In the course of the distillation, a mixture of piperidine and water distilled off azeotropically.

The distillation residue was brought to pH 3 by adding aqueous hydrochloric acid. The addition precipitated benzoic acid virtually quantitatively in the form of a very pure solid product. The benzoic acid was filtered off with suction and dried.

EXAMPLE 3

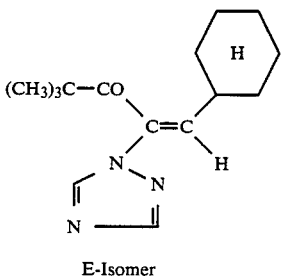

E-Isomer

A mixture of 1 mole of 3,3-dimethyl-1-(1,2,4-triazol-1-yl)-butan-3-one, 0.2 mole of benzoic acid, 1.15 moles of cyclohexanecarbaldehyde, 0.15 mole of piperidine and 250 g of isododecane was boiled at 65° C. under a pressure of about 20 mbar and under a water separator for 8 hours. When 20.7 ml of water had been separated off, the reaction mixture was worked up in the manner described in Example 2. This gave 230 g of a product which consisted to 98% of the E-isomer of 1-cyclohexyl-4,4-dimethyl-2-(1,2,4-triazol-1-yl)-1-penten-3-one. From this the yield can be calculated as being 86.4% of theory.

EXAMPLE 4

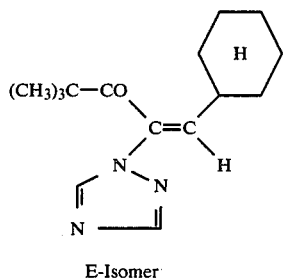

E-Isomer (With recycling)

A mixture of 1 mole of 3,3-dimethyl-1-(1,2,4-triazol-1-yl)-butan-3-one, 0.45 mole of cyclohexanecarboxylic acid, 1.3 moles of cyclohexanecarbaldehyde, 0.3 mole of piperidine and 300 g of isododecane was boiled at 60°-66° C. under a pressure of about 20 mbar and under a water separator for 10 hours. The apparatus were then flushed with nitrogen, 250 g of water were added to the reaction mixture, and the mixture was brought to pH 5 (aqueous phase) by adding concentrated hydrochloric acid. The mixture was stirred at 40° C. for 5 minutes and then brought to pH 12 by adding about 200 g of 10% sodium hydroxide solution, and the aqueous phase was separated off, while the organic phase was stirred at temperatures between −10° C. and 0° C. for 10 hours. The crystalline product formed in the organic phase was filtered off with suction, washed with 30 g of cold isododecane and dried under reduced pressure at 50° C. This gave 200 g of a product which consisted to 98% of the E-isomer of 1-cyclohexyl-4,4-dimethyl-2-(1,2,4-triazol-1-yl)-1-penten-3-one. From this the yield can be calculated as being 75% of theory.

The mother liquor was recycled. For this purpose, this alkaline aqueous phase was subjected to a distillation, a mixture of piperidine and water azeotropically passing into the receiving flask. The distillation residue was then brought to pH 3 by adding hydrochloric acid. The cyclohexanecarboxylic acid precipitating during this pH change in the form of an oil was separated off and combined with the mixture of piperidine and water and with the organic mother liquor. 2 g of piperidine and 4 g of cyclohexanecarboxylic acid were added, and the mixture was stripped of water by azeotropic distillation at 65° C. under reduced pressure. When the separation from water was complete, a mixture of 119 g of cyclohexanecarbaldehyde and 170.4 g of 3,3-dimethyl-1-(1,2,4-triazol-1-yl)-butan-3-one was added, and the resulting mixture was again boiled at 60°-66° C. under a pressure of about 20 mbar and under a water separator for 10 hours. Renewed working-up and crystallisation in the manner described above gave 284 g of a product which consisted to 96.5% of the E-isomer of 1-cyclohexyl-4,4-dimethyl-2-(1,2,4-triazol-1-yl)-1-penten-3-one. From this the total yield over the two cycles can be calculated as being 90% of theory.

The organic mother liquor produced and recovered piperidine as well as recovered cyclohexanecarboxylic acid were reused, small losses of cyclohexanecarbaldehyde, piperidine and cyclohexanecarboxylic acid being made good. Also, in order to avoid impurities accumulating in the organic mother liquor, 10-20% of the mother liquor was purged after each cycle.

This purged portion was likewise purified by first of all distilling off the isododecane and the cyclohexanecarbaldehyde under reduced pressure by means of a thin-film evaporator (jacket temperature: 140° C.; 2-5 mbar; temperature at the top: 80°-85° C.) and then distilling off a mixture of the E-isomer of 1-cyclohexyl-4,4-dimethyl-2-(1,2,4-triazol-1-yl)-1-penten-3-one, the corresponding Z-isomer, an isomer with shifted double bond as well as cyclohexanecarbaldehyde and 3,3-dimethyl-1-(1,2,4-triazol-1-yl)-butan-3-one (jacket temperature: 190°-200° C.; 1-2 mbar; temperature at the top: 148°-155° C.). The low-boiling portions and the product-containing distillate were returned to the reaction, while the bottom product was destroyed.

EXAMPLE 5

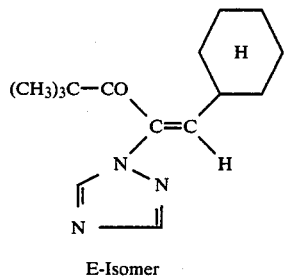

E-Isomer

A mixture of 1 mole of 3,3-dimethyl-1-(1,2,4-triazol-1-yl)-butan-3-one, 0.45 mole of benzoic acid, 1.3 moles of cyclohexanecarbaldehyde, 0.3 mole of piperidine and 300 g of isododecane was boiled at 62°-65° C. under a pressure of about 20 mbar and under a water separator for 8 hours. When 22.5 ml had been separated off, the mixture was worked up by flushing the apparatus with nitrogen, washing the reaction mixture with 100 g of 20% strength aqueous sodium hydroxide solution, and then cooling the aqueous phase to −10° C. and thoroughly stirring at this temperature for 4 hours. The resulting colourless crystals were filtered off with suction, washed with cold isododecane and dried at 50° C. under reduced pressure. This gave a product which consisted to 96% of the E-isomer of 1-cyclohexyl-4,4-dimethyl-2-(1,2,4-triazol-1-yl)-1-penten-3-one. The yield was 75% of theory.

The mother liquor was then washed first of all with 100 g of water and concentrated hydrochloric acid and then, until neutral, with 100 g of water and some drops of 20% sodium hydroxide solution. Cyclohexanecarbaldehyde and some solvent were then distilled off, and dimethylamine was added to the residue at temperatures between −5° C. and 0° C. The crystalline solid substance which had precipitated after stirring at −5° C. to 0° C. for several hours, was filtered off with suction, washed with a little isododecane and dried. This produced a further 36 g of a product which consisted to 96% of the E-isomer of 1-cyclohexyl-4,4-dimethyl-2-

(1,2,4-triazol-1-yl)-1-penten-3-one. The total yield was 87% of theory.

EXAMPLE 6

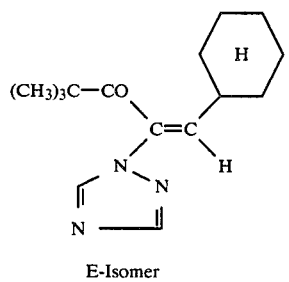

E-Isomer (As a recycling process)

1 mole of 3,3-dimethyl-1-(1,2,4-triazol-1-yl)-butan-3-one, 1 mole of cyclohexanecarbaldehyde and 54.9 g (0.45 mole) of recycled benzoic acid were added to a circulated mixture of 25.5 g (0.3 mole) of piperidine, 34.0 g (0.3 mole) of cyclohexanecarbaldehyde and 300 g of isododecane, and the resulting mixture was boiled under a pressure of 15–20 mbar and under a water separator for 8 hours. After the subsequent flushing of the apparatus with nitrogen, 10% strength sodium hydroxide solution containing 0.5 mole of sodium hydroxide was added to the reaction mixture. Some of the water required for preparing the sodium hydroxide solution came from that part of the preceding batch from which the piperidine was recovered. The aqueous phase was separated off, and by briefly heating under reduced pressure some of it was distilled over into a receiving flask as a mixture of piperidine and water, which was used again in the wash with sodium hydroxide solution in the next cycle of the recycling process. The benzoic acid was precipitated from the remaining bottom product by acidifying with hydrochloric acid to pH 2, was filtered off with suction and was used again in the next batch. The organic phase was cooled down and stirred at −10° C. to 0° C. for 2 hours. The resulting precipitate was filtered off with suction, washed with cold isododecane, and dried. This gave the E-isomer of 1-cyclohexyl-4,4-dimethyl-2-(1,2,4-triazol-1-yl)-1-penten-3-one in a yield of 85% of theory.

The mother liquor remaining when the E-isomer of 1-cyclohexyl-4,4-dimethyl-2-(1,2,4-triazol-1-yl)-1-penten-3-one was filtered off with suction had a purge stream taken from it and then had added the amount of cyclohexanecarbaldehyde and 3,3-dimethyl-1-(1,2,4-triazol-1-yl)-butan-3-one consumed in the reaction, and, after addition of recycled benzoic acid, was reintroduced into the recycling process.

EXAMPLE 7

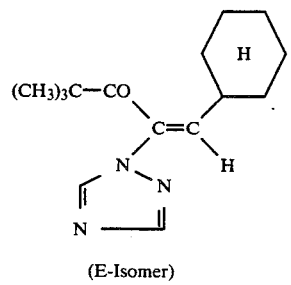

(E-Isomer)

The process was carried out in a 6 liter stirring apparatus equipped with an external circulating pump containing a glass column, which is filled with 1.6 kg of zeolite. The circulation of the material was achieved by means of a gear pump; the material was introduced into the glass column from below at a rate of about 25 to 30 liters per hour.

The following compounds were consecutively introduced into the apparatus:

1377 g (8.0 mole) of 3,3-dimethyl-1-(1,2,4-triazol-1-yl)-butan-3-one (purity: 97%).
1070 g (9.36 mole) of cyclohexanecarbaldehyde (purity: 98%).
180 g (1.47 mole) of benzoic acid
84 g (0.98 mole) of piperidine
1400 g of toluene
Total volume: about 4.1 liters at 70° C.

The mixture was heated, whilst stirring, by means of vapor up to a temperature of 65° C. After the solid materials had dissolved, the circulating pump was switched on, and the reaction mixture was maintained at a temperature of 69° to 71° C. for 9 hours. The reaction mixture was then transferred into a washing flask. The zeolite was extracted with 1,200 ml of toluene at a temperature of 70° C. for 30 minutes, and thereafter the toluene solution was combined with the reaction mixture. Subsequently, the zeolite was rinsed twice with, in each case, 1,200 ml of methanol in the same manner. The methanol phase was concentrated by distilling off the solvent, and the residue was also introduced into the washing flask.

The following operations were consecutively carried out in the washing flask:
1. Alkaline washing with 1,200 g of 5% aqueous sodium hydroxide solution.
2. Acidic washing with 10% aqueous sulphuric acid until the pH-value of the reaction mixture was 3 to 4.
3. Neutral washing with 1,000 g of water.

The organic phase was concentrated completely by means of a thin-film evaporator and the remaining residue was mixed within 1 minute, whilst stirring vigorously, with a mixture of
2,640 g of water,
264 g of a 40% solution of dimethylamine in water and
264 g of an emulsifier of the formula

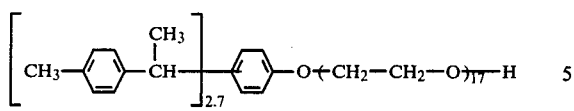

at room temperature. The resulting mixture was kept for 4 hours at a temperature of 20° to 22° C. and was then cooled to 5° C. The precipitate was filtered off with suction, washed twice with, in each case, 1,080 ml of cold water, and dried. This gave the E-isomer of 1-cyclohexyl-4,4-dimethyl-2-(1,2,4-triazol-1-yl)-1-penten-3-one in a yield of 1,856 g (88% of theory). Purity: 99%.

It will be understood that the specification and examples are illustrative, but not limitative of the present invention and that other embodiments within the spirit and scope of the invention will suggest themselves to those skilled in the art.

What is claimed is:

1. A process for preparing E-isomers of 1-cyclohexyl-2-(1,2,4-triazol-1-yl)-1-penten-3-one derivatives of the formula

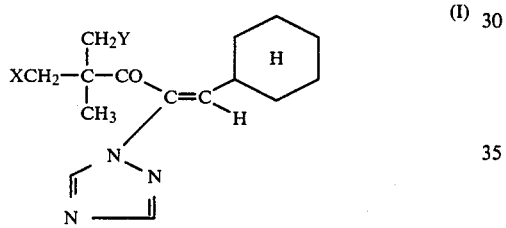

in which
X represents hydrogen and Y represents hydrogen fluorine or chlorine,
characterised in that triazolyl-ketones of the formula

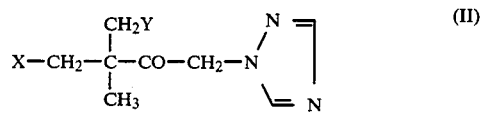

in which
X and Y have the abovementioned meaning, are reacted with an excess of cyclohexanecarbaldehyde of the formula

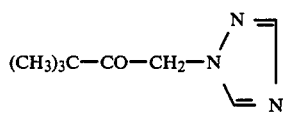

in the presence of a non-polar organic diluent selected from xylene, toluene, cyclohexane, ligroin, isooctane, dodecane or isododecane and in the presence of a catalyst mixture of an organic acid selected from acetic acid, propionic acid, pivalic acid, 2-ethylhexanoic acid, cyclohexanecarboxylic acid or benzoic acid and a secondary amine selected from dimethylamine, diethylamine, diisopropylamine, diisobutylamine, pyrrolidine, morpholine, hexahydro-1-H-azepine, piperidine, 2-methylpiperidine or 2,6-dimethylpiperidine in a molar ratio of 1:0.5 to 1:1 at temperatures between 40° and 100° C. by continuously removing the water formed and then either (a) an aqueous base is added to the reaction mixture, which, if appropriate after the aqueous phase has been separated off, is stirred at temperatures between −20° C. and +30° C., and the product precipitating in the form of crystals is separated off, or (b) the reaction mixture is treated in any order first of all with an aqueous mineral acid and an aqueous base and then washed with water, the organic phase is then concentrated by distilling out excess cyclohexanecarbaldehyde and solvent, the remaining residue, if appropriate after prior distillation, is reacted at temperatures between −20° C. and +30° C. with secondary amines, if appropriate in the presence of water and/or in the presence of a water-non-miscible solvent, and the product precipitating in the form of crystals in the course of the reaction is separated off.

2. A process according to claim 1, characterised in that 3,3-dimethyl-1-(1,2,4-triazol-1-yl)-butan-3-one of the formula $$(CH_3)_3C-CO-CH_2-N\begin{array}{c}N=\\ \\ \\=N\end{array}$$

is used as the triazolyl-ketone of the formula (II).

3. A process according to claim 1, characterised in that the reaction is carried out at temperatures between 50° C. and 80° C.

4. A process according to claim 1, characterised in that 1.1 to 1.8 moles of cyclohexanecarbaldehyde of the formula (III) are used per mole of triazolyl-ketone of the formula (II).

* * * * *